United States Patent [19]

Ruesch

[11] Patent Number: 4,491,009

[45] Date of Patent: Jan. 1, 1985

[54] ELECTRONIC CIRCUIT FOR VIBRATING TUBE DENSIMETER

[75] Inventor: James R. Ruesch, Boulder, Colo.

[73] Assignee: Micro Motion, Inc., Boulder, Colo.

[21] Appl. No.: 503,179

[22] Filed: Jun. 10, 1983

[51] Int. Cl.³ ............................................. G01N 9/00
[52] U.S. Cl. .................................................. 73/32 A
[58] Field of Search ..................... 73/32 A, 30, 861.38

[56] References Cited

U.S. PATENT DOCUMENTS

| | | |
|---|---|---|
| 2,943,476 | 7/1960 | Bernstein . |
| 3,339,400 | 9/1967 | Banks . |
| 3,420,092 | 1/1969 | Dorsch . |
| 3,456,491 | 7/1969 | Brockhaus . |
| 3,655,956 | 4/1970 | Ley . |
| 3,677,067 | 7/1972 | Miller et al. . |
| 3,690,147 | 9/1972 | Kuenzler . |
| 3,769,500 | 10/1973 | Schlatter . |
| 3,775,597 | 11/1973 | November . |
| 3,805,592 | 4/1974 | Miller et al. . |
| 3,808,875 | 5/1974 | Miller . |
| 3,842,655 | 10/1974 | Schlatter et al. .............. 73/32 A |
| 3,878,374 | 4/1975 | Schlatter . |
| 3,885,140 | 5/1975 | Schlatter . |
| 3,902,365 | 9/1975 | Knauth . |
| 3,910,101 | 10/1975 | Kratky et al. .................. 73/32 A |
| 4,011,746 | 3/1977 | Weitz, Jr. et al. . |
| 4,020,330 | 4/1977 | Bae . |
| 4,048,844 | 9/1977 | Dunikowski et al. . |
| 4,132,110 | 1/1979 | Muramoto ..................... 73/32 A |
| 4,170,128 | 10/1979 | Kratky et al. ............... 73/32 A X |

Primary Examiner—James L. Rowland
Assistant Examiner—Brian Tumm
Attorney, Agent, or Firm—Memel, Jacobs, Pierno & Gersh

[57] ABSTRACT

A method and electronic circuit for measuring the density of substances flowing through an oscillating container densimeter that measures the temperature of the oscillating container to determine the temperature coefficient of the spring constant about the axis of oscillation.

8 Claims, 3 Drawing Figures

ELECTRONIC CIRCUIT FOR VIBRATING TUBE DENSIMETER

BACKGROUND OF THE INVENTION

The present invention relates to electronically monitoring the mechanical oscillation characteristics of one or more resonantly vibrating tubes through which flowable substances are passing to determine the density of the substances. Both the temperature and natural period of oscillation of one or more resonantly oscillating tubes are electronically monitored, and the resulting signals are processed to accurately determine the density of the flowing substances independent of temperature variations.

It is known that one end of an elastic container can be rigidly mounted and that the other end of the cantilever mounted container can be oscillated at a resonant angular velocity. For such a spring-mass mechanical system, the resonant angular velocity of oscillation can be calculated by taking the square root of the ratio of the oscillating container's mass to its spring constant about the oscillation axis. Since the mass of the container will vary as the density of the substances flowing through the container varies, monitoring the resonant angular velocity of oscillation of a cantilever mounted container potentially offers a convenient means for measuring the density of flowable substances.

Various container configurations have been applied to the construction of oscillating container densimeters. Among these has been U-shaped flow tubes, with the tube rigidly mounted to a fixed base at the open ends of the U-shaped flow tube. Thus, by flowing a substance through the U-shaped flow tube and vibrating the tube at its resonant angular velocity the density of substances flowing through the U-shaped flow tube can be measured. A known improvement for the vibrating U-shaped flow tube densimeter is the use of a second cantilever mounted U-shaped flow tube which is positioned along side the first U-shaped flow tube so as to have both U-shaped flow tubes act as the times of a tuning fork. Among the advantages achieved by such tuning fork operation is substantial attenuation, at the base, of vibration forces associated with the driving of the U-shaped flow tubes at their resonant angular velocities of oscillation.

An additional variable which affects measurements of the density of flowable substances passing through oscillating container densimeters is the temperature of the oscillating container. For, the spring constants of an elastic container are dependent on temperature. This dependency on temperature and its effect on the determination of density by measuring resonant angular velocity of oscillation has been known. Previous attempts to address the dependency of the resonant angular velocity of oscillation on temperature variations have included those disclosed in U.S. Pat. Nos. 4,170,128 and 3,910,101. Disclosed in U.S. Pat. No. 4,170,128 is a mechanical arrangement incorporating a length of cord or string attached to a vibrating U-shaped flow tube. According to the disclosure in U.S. Pat. No. 4,170,128, the length of the string is dependent on temperature, and, therefore, the tension of the mounted string is varied by temperature. As further disclosed this variation in tension modifies the vibration characteristics of the U-shaped flow tube to compensate for temperature variations. Disclosed in U.S. Pat. No. 3,910,101 is an electrical circuit for both monitoring and controlling the oscillation of a fluid filled container. Included as a part of the disclosed circuit is a bridge circuit having as the variable element a temperature dependent sensor. The output of the bridge circuit according to the teachings in U.S. Pat. No. 3,910,101 is used to alter, according to fluctuations in temperature, both the phase and amplitude of the signal driving the oscillation of the fluid filled container.

The disclosures in both U.S. Pat. Nos. 4,132,110 and 3,910,101 are directed to the monitoring of temperature variations for the purpose of altering the mechanical oscillations of oscillating containers.

Unlike the previous two patents U.S. Pat. No. 4,132,110 discloses a mechanical configuration and electrical circuit for determining the density of a fluid passing through an oscillating container without a feedback system for altering the mechanical oscillations of the container as a function of temperature variations. The electrical circuitry disclosed in U.S. Pat. No. 4,132,110 for determining fluid density incorporates an oscillator to generate a standard signal from which is subtracted the signal representative of the motion of the oscillating container. According to the disclosures in U.S. Pat. No. 4,132,110, this difference signal is then combined with the signal from a temperature probe to provide a signal proportional to the density of the fluid being measured based on a reference temperature.

SUMMARY OF THE INVENTION

In order to make precise density measurements using an oscillating container densimeter a relationship must be developed which incorporates not only the resonant angular velocity of oscillation of the container and the mass of the substance passing through the container, but also the variation in the spring constant about the oscillation axis of the oscillating container. For temperature changes cause variations in the spring constants of elastic materials, and for many practical applications either or both the ambient environment or the flowing substance being measured can produce substantial temperature fluctuations. Therefore, in addition to the resonant angular velocity of oscillation the temperature of the oscillating container must also be measured, and the temperature dependent spring constant about the oscillation axis calculated.

It will be shown below that the equation for the density of a substance passing through a resonantly oscillating container is, in general, a relationship where the first term is the oscillating container's spring constant about the oscillation axis, which is a function of temperature, multiplied by the square of the period of oscillation for the oscillating container, with this product being divided by a first constant. The second, and last term of this equation, is a constant which is subtracted from the first term to give a direct calculation of density.

The present invention utilizes this analytical description of the mechanics of an oscillating container densimeter to provide an accurate method and electronic circuitry for directly determining the density of substances passing through the densimeter.

The measurement technique of the present invention is dependent on the outputs of two sensors which are mounted either on or in conjunction with the oscillating container. One of these sensors can be a velocity sensor, such as an electrical coil and magnet, which monitors the movement of the container and provides a sinusoidal signal corresponding to such movement. The other sensor can be a temperature variable resistor mounted on the container or in any other isothermal location relative to the container. Obviously, other sensor types could be used as long as (1) a signal is provided which corresponds to the movement of the container so that the resonant period of oscillation can be determined; and (2) a signal is provided which corresponds to the temperature of the container so that the temperature coefficient for the spring constant of the container about the oscillation axis can be determined.

The circuit of the present invention includes two integrators which are connected in series. An input to the first of these integrators is a reference voltage. The outputs of these two integrators are controlled by electronic switches so that the output from the second integrator is a function of the square of the time that the inputted reference voltage is integrated. The duration of time during which the integrators function is determined by the output of the sense coil monitoring the movement of the oscillating container so that the combined output from the integrators is a function of the square of the resonant period of oscillation of the container. Controlling the reference voltage inputted to the first integrator is a circuit incorporating a bridge, one arm of the bridge being the temperature variable resistor which is mounted on the container so that as the temperature of the container varies the reference voltage is accordingly varied, and, therefore, the output of the integrators represents a product of a temperature dependent function and the square of the period of oscillation of the resonantly oscillating container. By controlling the output of the bridge circuit, an accurate representation of the variation in the spring constant of the container about the oscillation axis as a function of temperature can be provided to the series integrator circuitry. Thus, the output of the integrators after passing through a buffer circuitry gives a direct readout of the density of substances passing through the densimeter.

BRIEF DESCRIPTION OF THE DRAWINGS

The various objects, advantages and novel features of the present invention will be more readily apprehended from the following detailed description when read in conjunction with the appended drawings, in which.

DETAILED DESCRIPTION OF THE INVENTION

Figure 1:
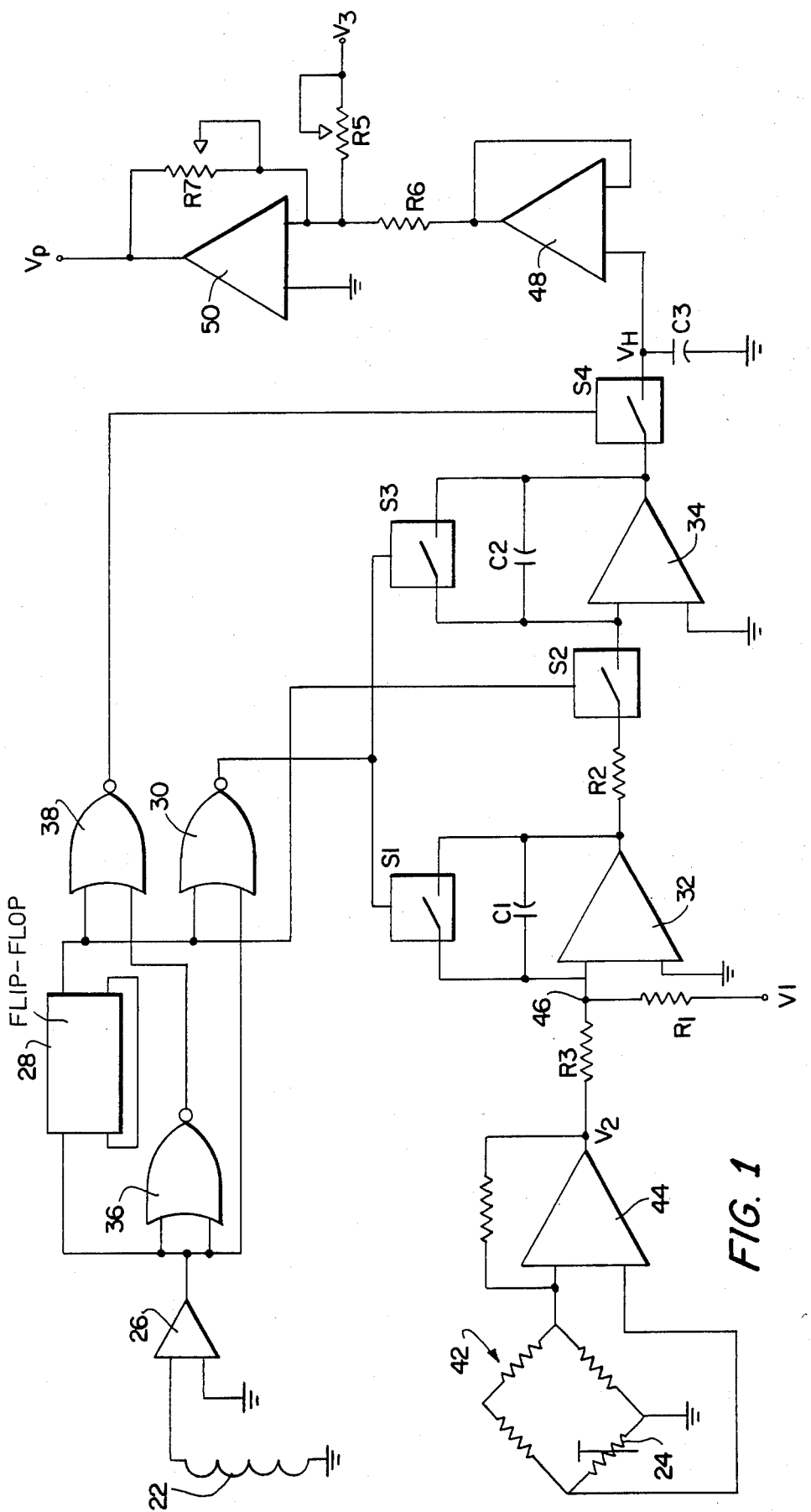
FIG. 1 is a block diagram of the electrical circuit of the present invention.

Referring now to the drawings, wherein corresponding components are designated by the same reference numerals throughout the various figures, a block diagram of the circuit of the present invention is shown in FIG. 1.

Figure 2:
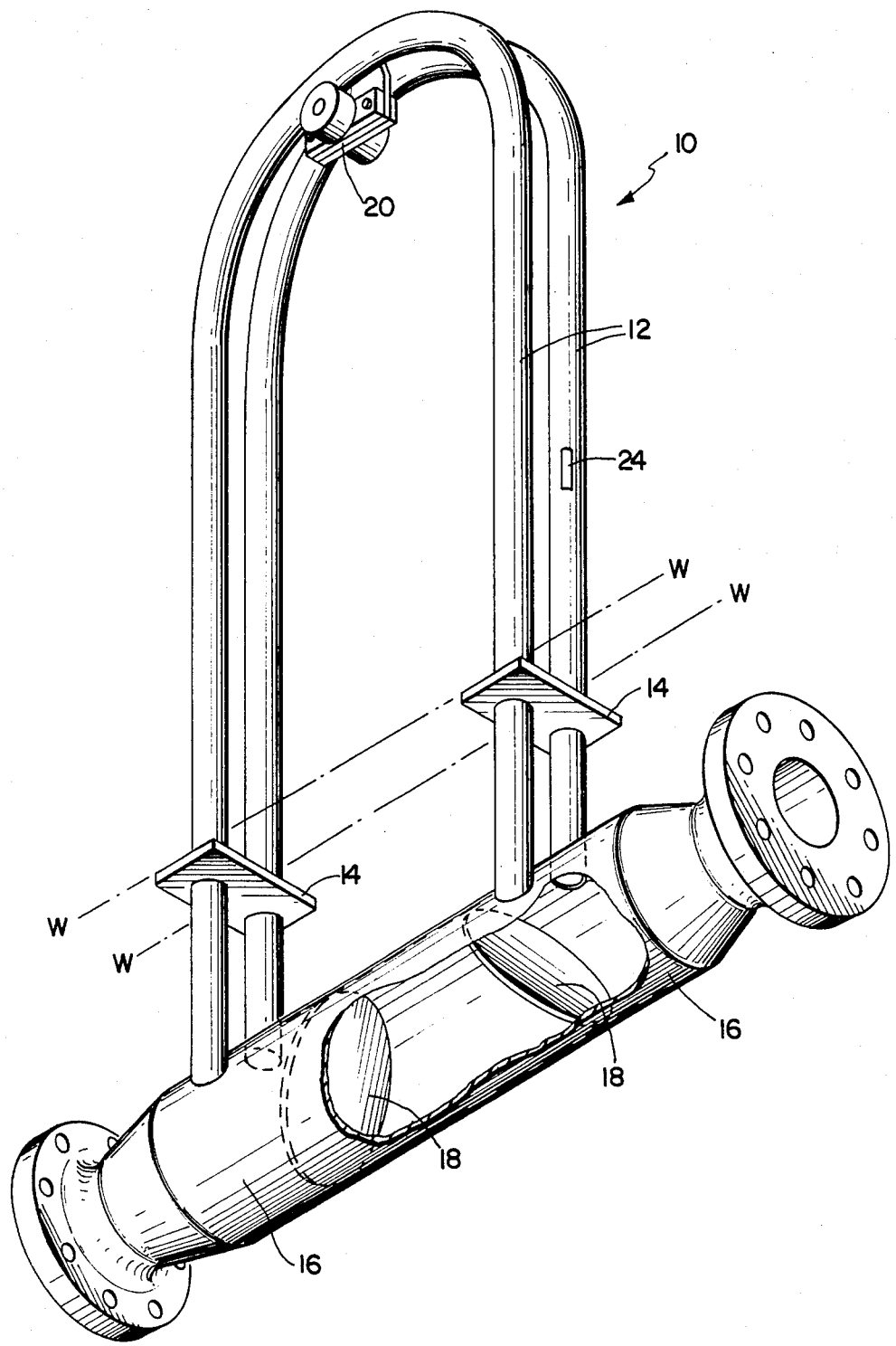
FIG. 2 is a perspective view of a twin vibrating tube densimeter with both motion and temperature sensors being mounted on the densimeter vibrating tubes; and, FIG. 3 is a graphical presentation of waveforms characteristic of the operation of the invention.
Figure 3:
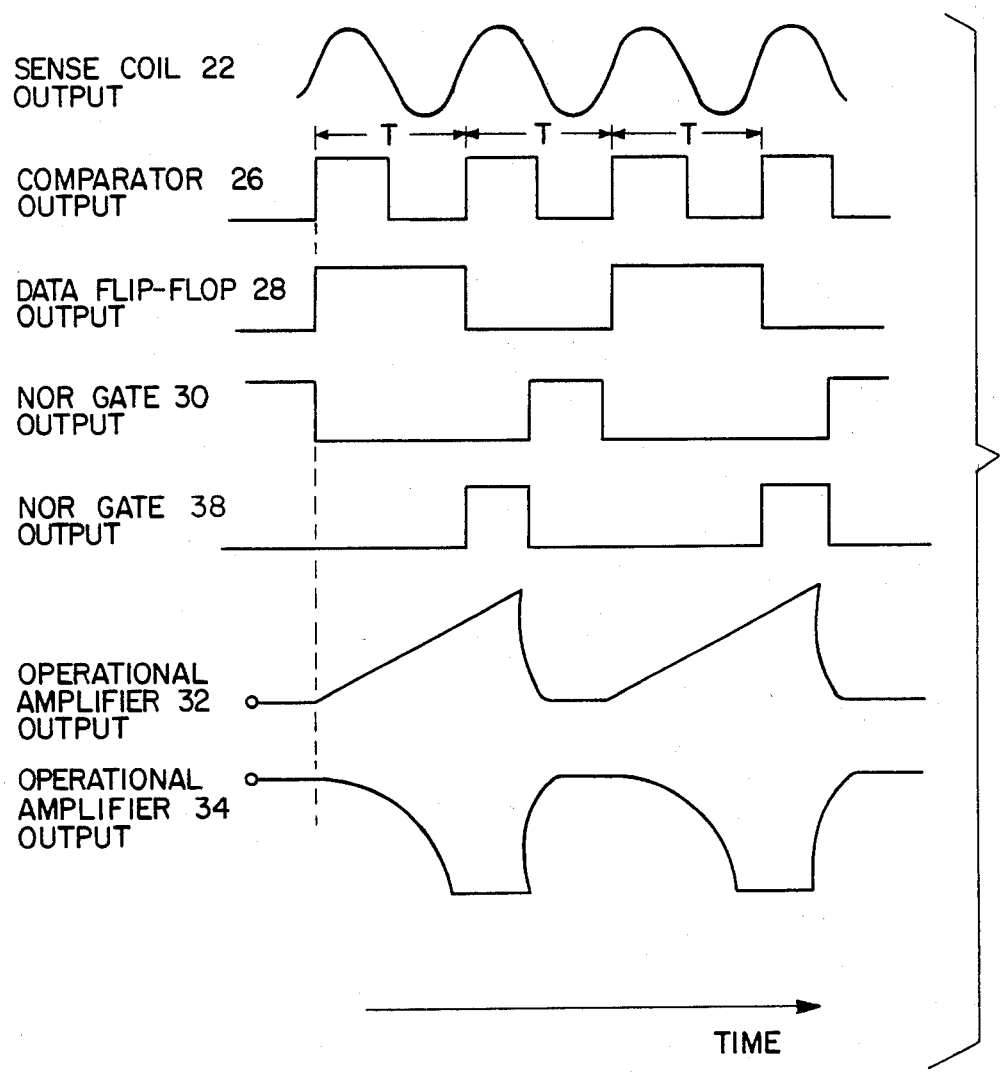

A densimeter, as generally designated by numeral 10, with two vibrating tubes 12, for which the electronic circuit of the present invention can be used, is shown in FIG. 2. The configuration of densimeter 10 includes the supports 14, the plenums formed by manifolds 16 and end plates 18, and the electromagnetic drive and sensor mechanism 20. Such a configuration provides for parallel fluid flow through the two tubes 12, which act as the tines of a tuning fork when vibrated. A detailed description of the construction and fluid dynamics associated with this configuration is set forth in detail in pending U.S. patent application Ser. No. 439,035, filed Nov. 3, 1982 for Parallel Path Coriolis Mass Flow Rate Meter by inventors James E. Smith and Donald Cage.

As is known in the art, electromagnetic drive and sensor mechanism 20 can consist of such known means as a magnet fixed to one of the vibrating tubes 12, and a drive coil along with a sense coil 22 fixed to the other of the vibrating tubes 12. As is also known in the art, by passing an oscillating electrical current through the drive coil the two tubes 12 can be sinusoidally driven about their respective bending axes, W—W, at their common resonant angular velocity of oscillation. Such oscillation will result in the tubes operating as the two tines of a tuning fork. As the tubes 12 resonantly oscillate an electrical signal correlating to the relative movement of tubes 12 is generated by the magnet and sense coil 22.

Irrespective of whether a single or multiple oscillating container structure is used, the solution for the equation of motion for a resonantly oscillating spring mounted mass is the same, and is accordingly applicable to the quantitative description of the mechanics of an oscillating container densimeter. This solution is $$\omega = \sqrt{K(t)/M} \qquad \text{(equation 1)}$$

where
  $\omega$ is the angular velocity of oscillation for the resonantly oscillating spring mounted mass,
  $K(t)$ is the spring constant about the oscillation axis and is a function of temperature t, and
  M is the mass affixed to the spring.

For a densimeter as shown in FIG. 2 the mass M is the sum of the masses of vibrating tubes 12, which can be identified as $M_T$, plus the mass of the substance flowing through the vibrating tubes 12, which can be identified as $M_F$. Therefore, $$M = M_T + M_F$$

The mass of the substance flowing through the vibrating tubes 12 is equal to the product of the density, $\rho$, of the substance times the internal volume, $V_o$, of the vibrating tubes 12.

$$M_F = \rho V_o$$

Substituting the last relation into equation 1 and solving for density results in the following:

$$\rho = \frac{K(t)}{4\pi^2 V_o} T^2 - \frac{M_T}{V_o} \qquad \text{(equation 2)}$$

Where t is the period of oscillation of the resonantly vibrating tubes 12. Noting that on the right side of equation 2 all of the quantities except for the period of oscillation, T, and the spring constant, K(t), which is a function of temperature, are constants permits rewriting of equation 2 in the following useful format.

$$\rho = \frac{K(t) T^2}{K_1} - K_2 \qquad \text{(equation 3)}$$

where $K_1$ and $K_2$ are constants.

to determine the accuracy of the readings provided by the circuitry of the present invention.

TABLE II

| Fluid | Circuit Readout | Published Specific Gravity |
| --- | --- | --- |
| Isopropanol Alcohol | 0.79 | 0.7855 |
| Tetrabromoethane | 2.96 | 2.9656 |
| Distilled Water | 0.99 | 0.9982 |

The above discussion and related illustrations of the present invention are directed primarily to preferred embodiments and practices of the invention. However, it is believed that numerous changes and modifications in the actual implementation of the concepts described herein will be apparent to those skilled in the art, and it is contemplated that such changes and modifications may be made without departing from the scope of the invention as defined by the following claims.

What is claimed is:

1. An electronic circuit for measuring the density of substances flowing through a resonantly oscillating container by determining the mass of said substances, comprising:
   (A) a temperature to electric transducer electrically connected to an electric signal measurement circuit means for generating an electric signal having a magnitude determined by the temperature of said container; and,
   (B) a mechanical to electric transducer for generating an electrical output signal having a magnitude determined by the movement of said container, the electrical output signal of said mechanical to electric transducer being electrically connected to an electronic logic circuit means for controlling an electrical output signal of an electronic integrator circuit means so that the magnitude of the electrical output signal from said electronic integrator circuit means is determined by the square of the period of oscillation of said container;
   whereby the density of the substances flowing through said resonantly oscillating container is determined by measuring the magnitude of the electrical output signal from said electronic integrator circuit means when the electric signal having a magnitude determined by the temperature of said container is inputted to said electronic integrator circuit means.

2. An electronic circuit as set forth in claim 1 in which said temperature to electric transducer is a temperature variable resistor.

3. An electronic circuit as set forth in claim 2 in which said electric signal measurement circuit used for measuring the resistance of said temperature to electric transducer includes a bridge circuit one branch of which is said temperature to electric transducer.

4. An electronic circuit as set forth in claim 1 in which said mechanical to electric transducer is a coil and magnet with said coil and magnet moveable relative to each other in coincidence with the oscillation of said container.

5. An electronic circuit as set forth in claim 1 in which said electronic integrator circuit means includes two electronic integrator circuits connected in series.

6. A method of measuring the density of substances flowing through a resonantly oscillating container by determining the mass of said substances, comprising:
   (A) measuring the temperature of said container and generating an electrical signal having a magnitude determined by said temperature;
   (B) measuring the period of oscillation of said container and controlling the time of integration of an electronic integrator circuit means so that the output of said electronic integrator circuit means represents the square of said period of oscillation; and.
   (C) electrically connecting to the input of said electronic integrator circuit means said electrical signal having a magnitude determined by the temperature of said container;
   whereby the density of the substances flowing through said resonantly oscillating container is determined by measuring the output of said electronic integrator circuit means.

7. A method of measuring density as set forth in claim 6 in which the temperature of said container is measured with a temperature variable resistor connected to a branch of a bridge circuit.

8. A method of measuring density as set forth in claim 6 in which said electronic integrator circuit means includes two electronic integrator circuits connected in series.

* * * * *

UNITED STATES PATENT AND TRADEMARK OFFICE
CERTIFICATE OF CORRECTION

PATENT NO. : 4,491,009

DATED : January 1, 1985

INVENTOR(S) : James R. Ruesch

It is certified that error appears in the above-identified patent and that said Letters Patent is hereby corrected as shown below:

Column 1, line 41, delete "times", and insert "tines" therefor.

Signed and Sealed this

Sixth Day of August 1985

[SEAL]

*Attest:*

DONALD J. QUIGG

*Attesting Officer*    *Acting Commissioner of Patents and Trademarks*